(12) United States Patent
Cole (10) Patent No.: US 7,551,278 B2
(45) Date of Patent: Jun. 23, 2009

(54) FLUID LIGHT GUIDE SYSTEM

(75) Inventor: Barrett E. Cole, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 287 days.

(21) Appl. No.: 11/383,166

(22) Filed: May 12, 2006

(65) Prior Publication Data

US 2007/0263216 A1 Nov. 15, 2007

(51) Int. Cl.
*G01N 21/00* (2006.01)

(52) U.S. Cl. .......................... 356/338; 356/340

(58) Field of Classification Search ............. 422/82.05, 422/82.09; 356/39, 335–343, 246; 250/559.4, 250/559.42; 600/309, 310, 322, 317, 308
See application file for complete search history.

(56) References Cited

U.S. PATENT DOCUMENTS

| | | | |
|---|---|---|---|
| 3,995,934 A * | 12/1976 | Nath | ........................... 385/125 |
| 4,286,839 A | 9/1981 | Ilzig et al. | |
| 4,711,126 A | 12/1987 | Houpt et al. | |
| 4,962,986 A | 10/1990 | Hompel et al. | |
| 5,573,531 A | 11/1996 | Gregory | |
| 5,608,834 A | 3/1997 | Van Leeuwen | |
| 5,717,807 A | 2/1998 | Theroux et al. | |
| 5,836,750 A | 11/1998 | Cabuz | |
| 5,859,946 A | 1/1999 | Wojcik et al. | |
| 6,597,438 B1 | 7/2003 | Cabuz et al. | |
| 6,970,245 B2 | 11/2005 | Fritz et al. | |
| 6,983,093 B2 | 1/2006 | Fraval et al. | |
| 7,245,379 B2 * | 7/2007 | Schwabe | ..................... 356/436 |

FOREIGN PATENT DOCUMENTS

| | | |
|---|---|---|
| GB | 2383127 | 6/2003 |
| WO | 2005033654 | 4/2005 |

OTHER PUBLICATIONS

LaserFocusWorld, "Laser Focus World—Research center combines photonics and fluidics," 3 pp. http://laserfocusworld.printthis.clickability.com, printed Apr. 20, 2006.
Brown et al., "Optical Waveguides Via Viscosity-Mismatched Microfluidic Flows," Applied Physics Letters 88, 1304109, 2006.
Kou et al., "On-chip Optical Components and Microfluidic Systems," Science Direct, Microelectronic Engineering, 73-74, pp. 876-880, 2004.

(Continued)

*Primary Examiner*—Gregory J Toatley, Jr.
*Assistant Examiner*—Tri T Ton
(74) *Attorney, Agent, or Firm*—Kris T. Fredrick (57) ABSTRACT

A system having a flow channel for conveying a sample and having fluid light guides for projecting light to the sample target area and collecting light from the sample target area. The system may have fluid light guides on or off the card containing the flow channel. Accurate alignment may be provided by the fluid light guides in lieu of requiring precise alignment for the light source and detectors. The flow channel may be part of a cytometer system.

1 Claim, 9 Drawing Sheets

OTHER PUBLICATIONS

Lien et al., "Monolithically Integrating Photonic and Microfluidic Devices Using a Self-Aligned Process," IEEE, pp. 525-526, 2003.

Lee et al., "Micro Flow with buried SU/8/SOG Optical Waveguides," Sensors and Actuators, A 103, pp. 165-170, 2003.

Vezenov et al., "Integrated Fluorescent light Source for Optofluidic Applications," Appled Physics Letters 86, 041104, 2005.

Wolfe et al., "Dynamic Control of Liquid-Core/Liquid-Cladding Optical Waveguides," PNAS, vol. 101, No. 34, pp. 12434-12438, Aug. 24, 2004.

* cited by examiner

FLUID LIGHT GUIDE SYSTEM

BACKGROUND

The invention pertains to particle detection and analysis, and particularly to light impingement of particles and light scattering by particles. More particularly, the invention pertains to the guiding of light to and from such particles.

Patents and applications related to the present invention may include: U.S. Pat. No. 6,597,438, issued Jul. 22, 2003, and entitled "Portable Flow Cytometry"; U.S. Pat. No. 6,970,245, issued Nov. 29, 2005, and entitled "Optical Alignment Detection System; U.S. Pat. No. 5,836,750, issued Nov. 17, 1998, and entitled "Electrostatically Actuated Mesopump Having a Plurality of Elementary Cells"; U.S. patent application Ser. No. 11/027,134, filed Dec. 30, 2004, and entitled "Optical Detection System with Polarizing Beamsplitter; U.S. patent application Ser. No. 10/908,543, filed May 16, 2005, and entitled "Cytometer Analysis Cartridge Optical Configuration"; and U.S. patent application Ser. No. 10/908,014, filed Apr. 25, 2005, and entitled "A Flow Control System of a Cartridge"; all of which are hereby incorporated by reference.

The invention is a fluid mechanism for guiding light to a target and containing light scattered by the target.

DESCRIPTION

Application of the present invention may include use in a cytometer flow channel with laser light particle analysis. Laser light may be scattered by the particles in the flow channel to determine the presence and properties of a particle. For instance, information about brightness of the scattered light may be used to determine the size of a particle scattering the impinging light. However, there appears to be no reasonable and practical way in the art to accurately guide the light to an intersection of particles in the flow channel, for example, blood cells on a cytometer card flow channel.

The light may be confined to a channel on or off a card by controlling the flow of immiscible fluids with light from a VCSEL or other laser source being directed down a middle of the channel. By tapering the channel, it is possible to direct the light with the fluids into the flow channel to within a micron. It may also be possible to collect the scattered light into another flow channel that is precisely oriented to collect over only a certain angle. This light may then be similarly fluid guided and delivered to a detector mounted, for instance, on the card periphery. Herein, fluids may mean liquids and/or gases.

Fluidic channels may be formed in a card by micromachining or replica molding. This may be done at a high resolution of better than 0.1 micron. The flow channels for the blood and light may be in the same place. The vertical position may be fixed by an accurate positioning of all of the channels.

The detector may be positioned to pick up light at an angle relative to the flow stream in a channel. The fluids may guide the scattered light to the detector much like an optical fiber with transparent materials having different indices of refraction. The fluids similarly have different indices of refraction.

The pump for moving the fluids around the light in a structure for containing the fluids may likewise be off the card like the light source and the detector. However, the fluids for light control may come from a reservoir on the card. Also, the pump for the fluids may be on the card. The pump may be a micro pump such as a mesopump. The fluid reservoir, pump and fluid on a card may be designed for short duration use because the card may be thrown away.

The fluid control apparatus for detected light may be optional. The detector may pick up the scattered light at an angle relative to the direction of the impinging light.

Light transmission and detection may be to and from the edge of the card. The position of the light source and detector would be like looking into the edge of the card.

The fluids in a containing structure may have one fluid being like a sheath over another fluid. This fluid may have a laminar flow or layer like form relative to the other fluid. The flow of the fluids should have no turbulence, i.e., a low Reynolds number.

There may be a sort of self-registration with the laser and the detector. The fluid may be injected. The laser source and detector may be calibrated relative to each other on the card. Fluid control of the source light and detected light may be built into the card. Then an external laser and detector could just then be coarsely aligned relative to the card itself. The fluid control on or of the card may be used for precise alignment of the impinging and scattered light with the flow channel and detector, respectively. In conjunction with flow control, there may be a controller connected to the fluid pumps and other fluid control apparatuses. The fluid may be injected from the inside or outside according to the kind of light control desired.

The fluid control of light may be applied to a fluorescence scheme of a cytometer or other kind of particle analysis equipment. The laser and detection may be to and from via the edge of the card, or it may to and from a broad surface of the card. The idea of fluid control of the light is that two fluidic layers have an index of refraction difference and this traps the light inside the inner fluid where it can be directed precisely to a target, for example, in a cytometer or other card. Scattered light, for instance, may be directed to a detector via another channel. The location of the channels may make for precise determination on the card of the light paths. The flow channels and the light channel may be in the same plane of the card.

Figure 1:
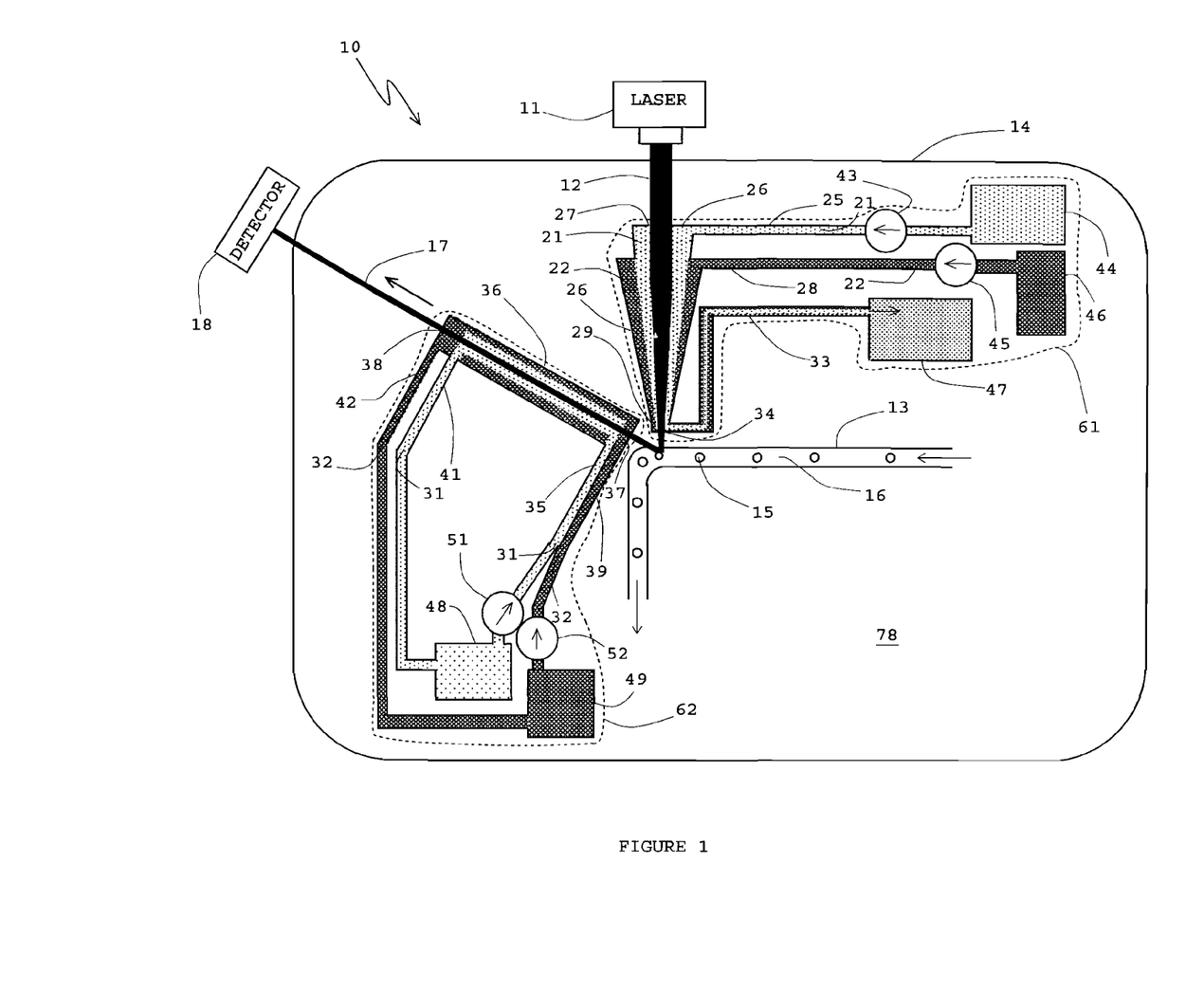
FIG. 1 shows an illustrative example of an on-card arrangement for fluid guiding of light to and from a flow channel on the same side of the flow channel.

In a fluid light guide system 10 of FIG. 1, a laser 11 may provide a light beam 12 to a flow channel 13 on a card 14. The light beam may impinge the flow channel 13 from the edge of card 14. Flow channel 13 may contain a stream of particles 15 that may be detected and analyzed. One illustrative application of the present invention may be a cytometer.

A flow stream 16 with a single file of particles 15 moving through the flow channel 13 may be impinged with a laser light beam 12. The particles 15 that are impinged by beam 12 may scatter some of the light 12 into scattered light 17 which may sensed by a detector 18.

The light 12 from laser 11 may be shaped and controlled into a smaller beam that is sufficient to enter the small flow channel 13 containing the flow stream 16 having particles 15. The light beam 12 may be focused or narrowed down with a fluid 21 around it. There may be a second layer of fluid 22 around the first layer of fluid 21. Fluid 22 may have a sheathing effect on fluid 21. These fluids may have a narrowing effect on the laser beam 12. The may control the focus and the beam 12 direction to a very specific point such as a target area of a flow channel 13 where particles 15 can flow through and be impinged by a tightly focused beam 12. The refractive indices of fluids 21 and 22 may be different. These fluids 21 and 22 of different indices proximate to each other in a concentric fashion may resemble an optical fiber designed to convey light.

Fluid 21 may enter a port 25 of a containing structure 26 which may have a window 27 for entry of laser beam 12. The fluid 21 may move through container 27 toward the flow channel 13 of card 14. The other fluid 22 may be brought into container 26 at an entry port 28 closer than port 25 to the flow channel 13. Fluid 22 may be like a sheath that wraps around fluid 21. Fluid 21 may be regarded as wrapping around beam 12. Containing structure 26 may have a circular cross section and be cone-shaped. Container 26 may have a narrowing structure in a direction toward the channel 13. That may cause the fluids 21 and 22 to narrow in toward the end 29 of container 26. The beam 12 may be similarly narrowed as it approaches the end 29 of structure 26. The fluids 21 and 22 may be diverted out of the structure 26 at the end 29 into an exit port 33, which are returned to a reservoir 47. Reservoir 47 may be segmented to hold fluids 21 and 22 together or separately, and if separately can be a resource of fluids 21 and 22 to reservoirs 44 and 46, respectively, or a resource of fluids 21 and 22 for pumps 43 and 45, respectively. On the other hand, fluids 21 and 22 may be returned directly from structure 26 to reservoirs 44 and 46, respectively. The focused and narrowed beam may proceed out the end 29 through a window 34 into the flow channel 13. Fluids 21 and 22 may be pumped into ports 25 and 28, respectively, by the pumps 43 and 45. Containing structure 26, pumps 43 and 45, and reservoirs 44, 46 and 47 may be situated in card 14. The fluid shaping assembly for laser beam 12 may be referred to a fluid guided source sub-system 61.

Light 17 is light 12 scattered by particles 15 in flow channel 13, and exiting the flow channel, which may be controlled by a set of fluids 31 and 32 having different indices refraction in a fashion similar to fluids 21 and 22 but in a parallel concentric fashion which is different in that sense than the conical concentric fashion of fluids 21 and 22. Fluid 31 may enter a port 35 which conveys the fluid to an elongated structure 36 having a cylindrical shape. The structure could have another shape. At an end of the structure 36 closest to the channel 13 may be a window 37 through which scattered light 17 from the flow channel 13 may enter. The light 17 may traverse the elongated structure 36 to the other end and exit the structure through a window 38. Light 17 may go from structure 36 to a detector 18. Fluid 31 may help contain the scattered light 17 into a more focused and controlled beam for reasons of more effective detection of the scattered light. Also, to assist in the containment of fluid 31 and light 17 is a fluid 32 having a different index of refraction than the index of fluid 31. Fluid 32 may enter elongated structure 36 through a port 39.

Fluid 32 may act as a sheath fluid around fluid 31 as the fluids flow through structure 36, provide an effective concentric containment and guide light 17 in a manner like that of an optical fiber having two media as concentric layers of a core for containment and guidance of the light through the fiber. The fluids 31 and 32, after traversing the length of elongated structure along with the light 17, may exit the structure via ports 41 and 42 and enter reservoirs 48 and 49, respectively. Pumps 51 and 52 may move the fluids 31 and 32, respectively, through structure 36. The fluids 31 and 32 may be returned to a common reservoir, separated into two compartments or not, like that for fluids 21 and 22. Pumps 51 and 52 may be micro pumps, e.g., mesopumps, in the card 14. The fluid shaping assembly for light 17 may be regarded as a fluid guided detection sub-system 62.

The velocity and pressures of fluids 31 and 32 may be adjusted to provide a variable control and guidance of light 17. The control of light 17 by the fluids 31 and 32 is not just for guiding the light but may be for self-registration and calibration.

Figure 1A:
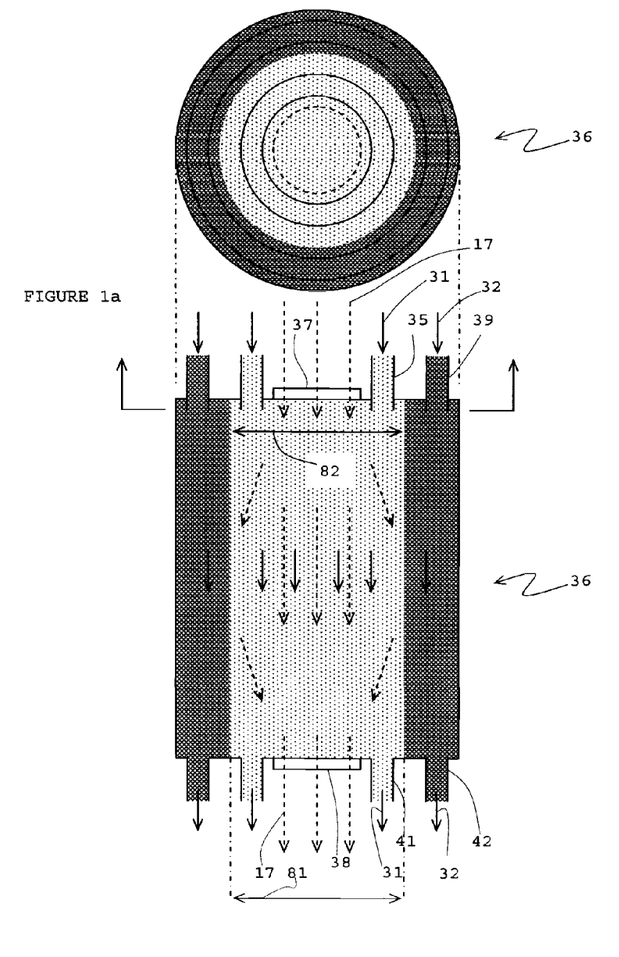
FIG. 1a reveals cross-sectional views of a fluid light guide.

FIG. 1a shows cross-sectional views of the dynamic fluid light guide mechanism 36. The design and principle of mechanism as illustrated in this Figure may be similar to that of the dynamic fluid light guide structure or mechanism 26. The dimensions 81 and 82 indicate the sheath or laminar barrier between the two fluids which may have different indices of refraction. The two fluids do not necessarily mix (i.e., immiscible) and may flow side by side with a smooth interface. Dimensions 81 and 82 may change in accordance with pressures and the velocities of the fluids 31 and 32, respectively. Dimensions 81 and 82 may be increased or decreased relative to the dimensions as illustrated. Also, dimensions 81 and 82 may be different from each other, or may be varied relative to each other. At the input portion of the structure 36, there may be a manifold or structural design so as, with fluids being input to ports 35 and 39, to cause two or more concentric layers of the fluids to flow through mechanism 36, the fluids having the same or various velocities and different indices of refraction. The inner (i.e., core) fluid 31 may have a higher index of refraction than the outer (i.e., sheath or cladding) fluid 32. The inner fluid 31 may convey the light 17 and the outer fluid 32 may contain the light within the inner fluid. There may be a manifold or manifolds connected between external ports 35 and 39 and the body of mechanism 36 that distribute the fluids in a concentric volume manner or other fashion in the mechanism 36. Also, there may be a manifold or manifolds that collect the fluids for removal via ports 41 and/or 42 from the mechanism 36. Either end of mechanism 36 may be of another shape beside circular. Also, mechanism 36 may be of another design beside cylindrical.

Figure 2:
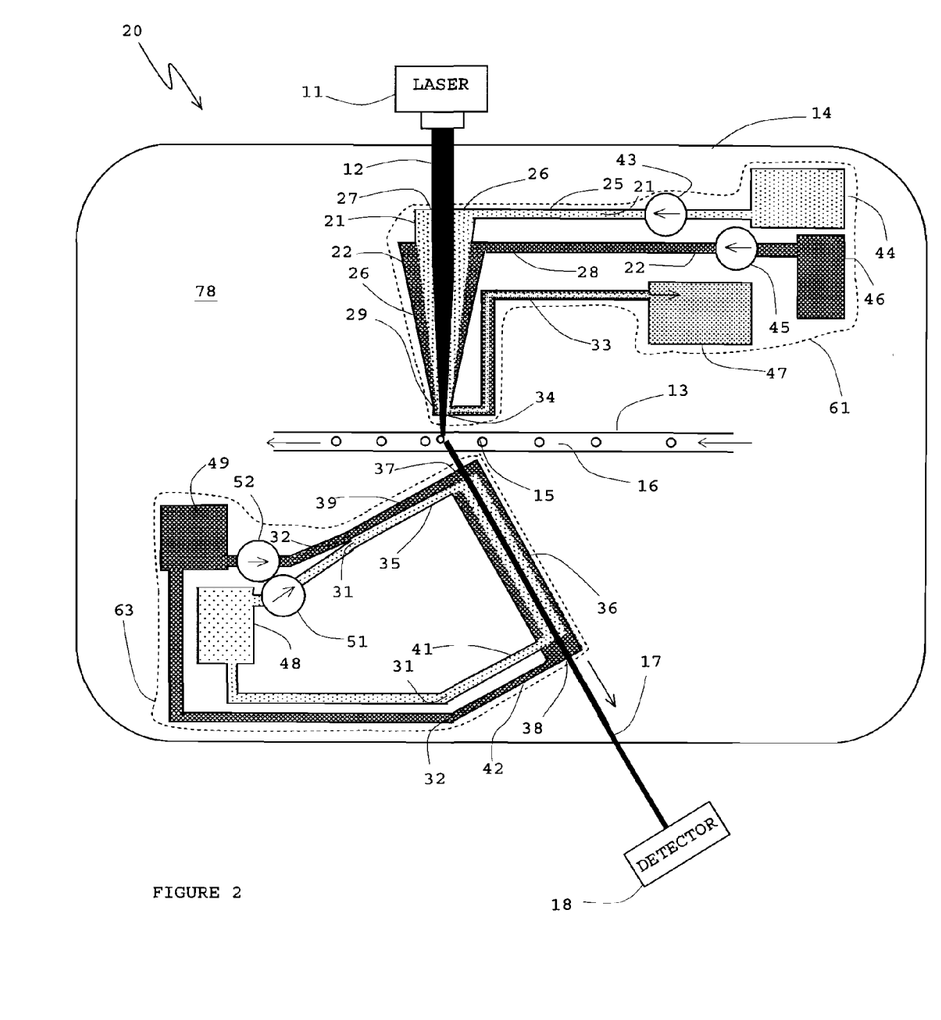
FIG. 2 shows an illustrative example of an on-card arrangement for fluid guiding of light to and from a flow channel on the opposite sides of the flow channel.

FIG. 2 shows a fluid light guide system 20. The fluid guided source sub-system 61 of system 10 may be used in system 20. This system 20 may be similar to system 10 except that the fluid guided detection sub-system 63 of system 20 is positioned differently than the fluid guided detection sub-system 62 of system 10. The sub-system 62 is positioned to collect light 17 from the same side of the channel 13 that the light source 11 and the light source sub-system 61 are situated. The sub-system 63 is positioned to collect light 17 from the opposite side of the channel 13 from where the light source 11 and the light source sub-system 61 are situated. However, the fluid guided sub-systems 62 and 63 are similar.

Figure 3:
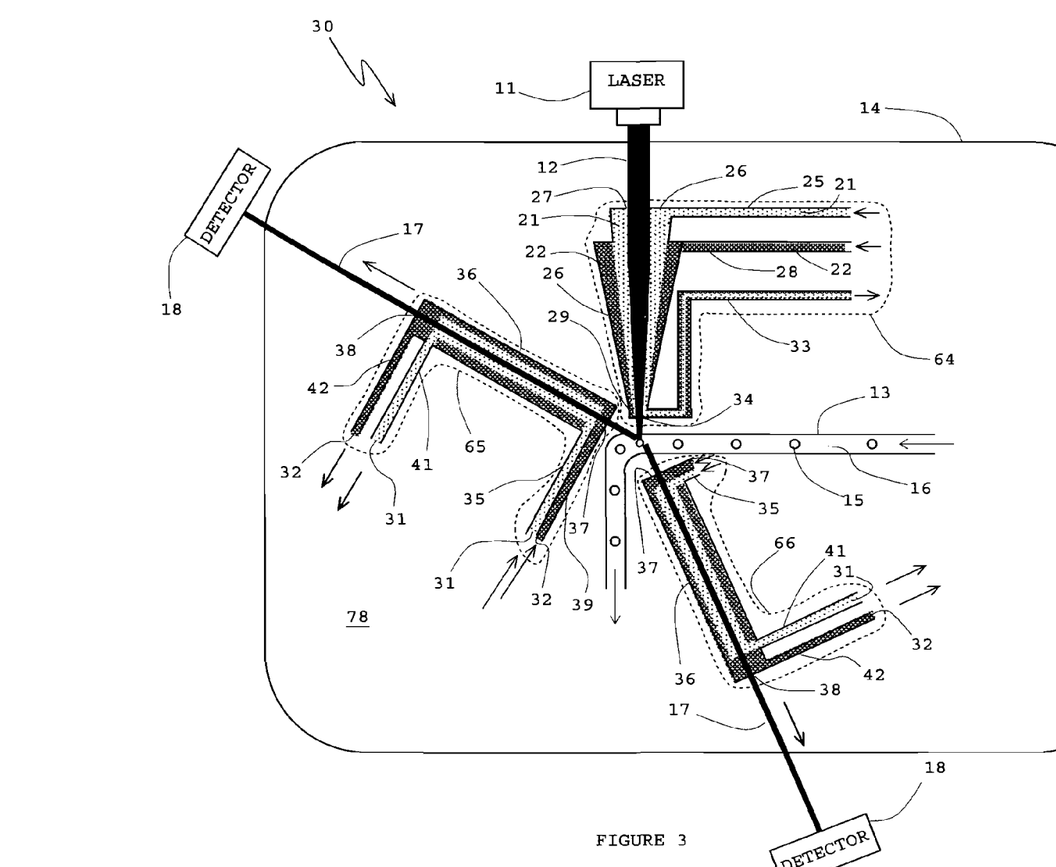
FIG. 3 shows an illustrative example of an on-card arrangement for fluid guiding of light to and from a flow channel both on the same side and opposite sides of the flow channel.

FIG. 3 shows a fluid light guide system 30. This system 30 has a fluid guided source sub-system 64 that is similar to the fluid guided source sub-system 61 of systems 10 and 20. The fluid guided detection sub-system 65 is positioned similarly as the fluid guided detection sub-system 62 of system 10, that is, on the same side of channel 13 as the source sub-system. The fluid guided detection sub-system 66 may be positioned similarly as the fluid guided detection sub-system 63 of system 20, that is, on the opposite side of channel 13 relative to the source sub-system. The detection sub-systems 65 and 66 and the source sub-system of system 30 are the same as the detection sub-systems 62 and 63 and the source sub-system 61 of systems 10 and 20, respectively, except that the on-card sub-systems of system 30 do not necessarily have pumps and reservoirs situated in the card 14.

Figure 4:
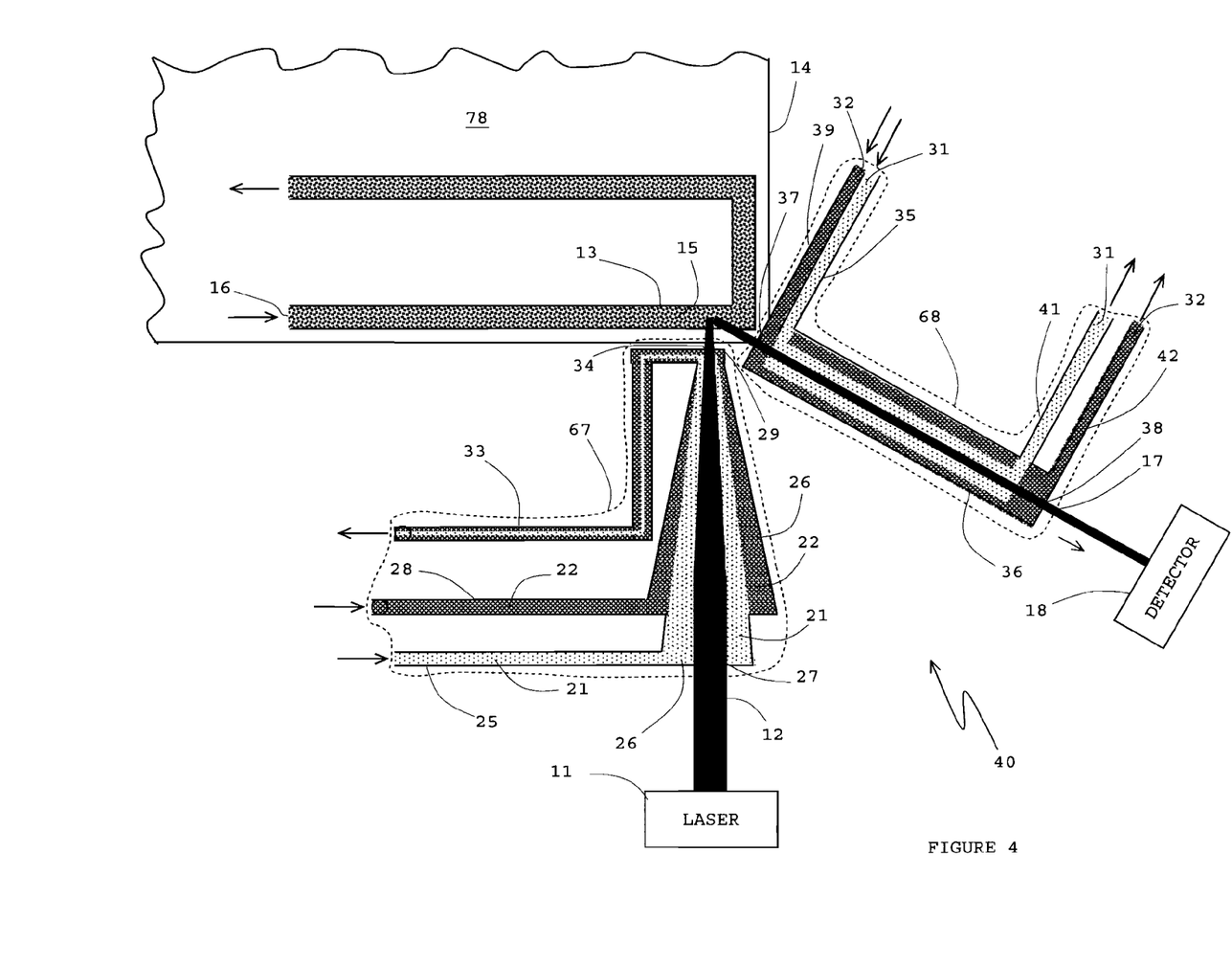
FIG. 4 shows an illustrative example of an off-card arrangement for guiding of light to and from a flow channel via an edge of a card.

System 40 of FIG. 4 reveals a card 14 with a channel 13 for a flow 16 of a sample and particles 15 which may be impinged with light 11 from a laser 11. Light 17 may be scattered by the particles 15 and detected by detector 18. In a manner like that of systems 10, 20 and 30 of FIGS. 1-3, the light beams 12 and 17 may be controlled with fluid control sub-systems 67 and 68, respectively. A difference between the sub-systems 67 and 68 and those of systems 10, 20 and 30 is that the sub-systems of system 40 are located off the card 14.

Figure 5:
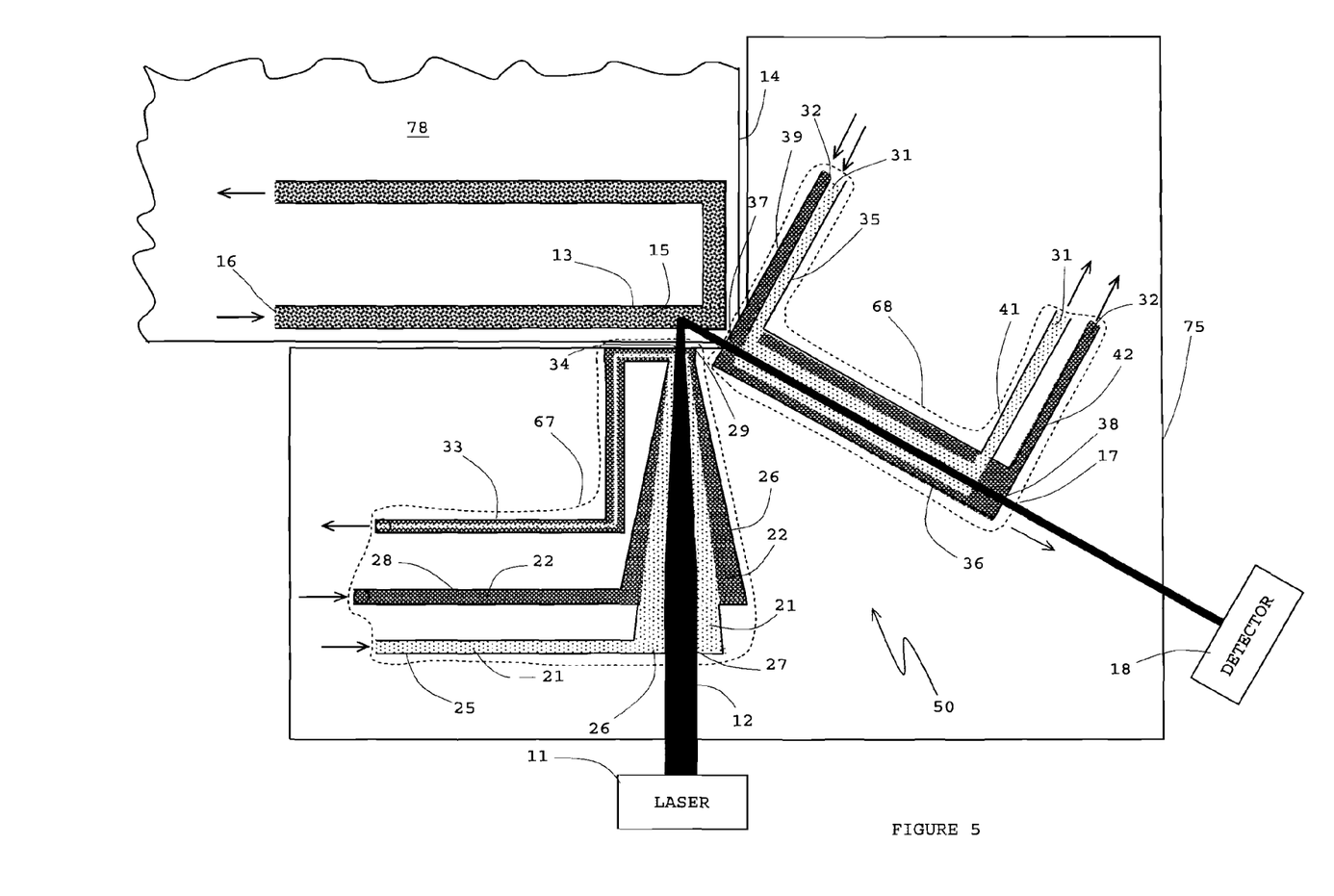
FIG. 5 shows an illustrative example of an off-card arrangement for fluid guiding of light to and from a flow channel with the fluid guiding on another card.

FIG. 5 shows a system 50 that has sub-systems 67 and 68 like those of system 40 in FIG. 4 except that sub-systems of system 50 are shown to be situated on another card 75 independent of card 14. The sub-systems of system 40 are not necessarily situated on a card external to card 14.

Figure 6:
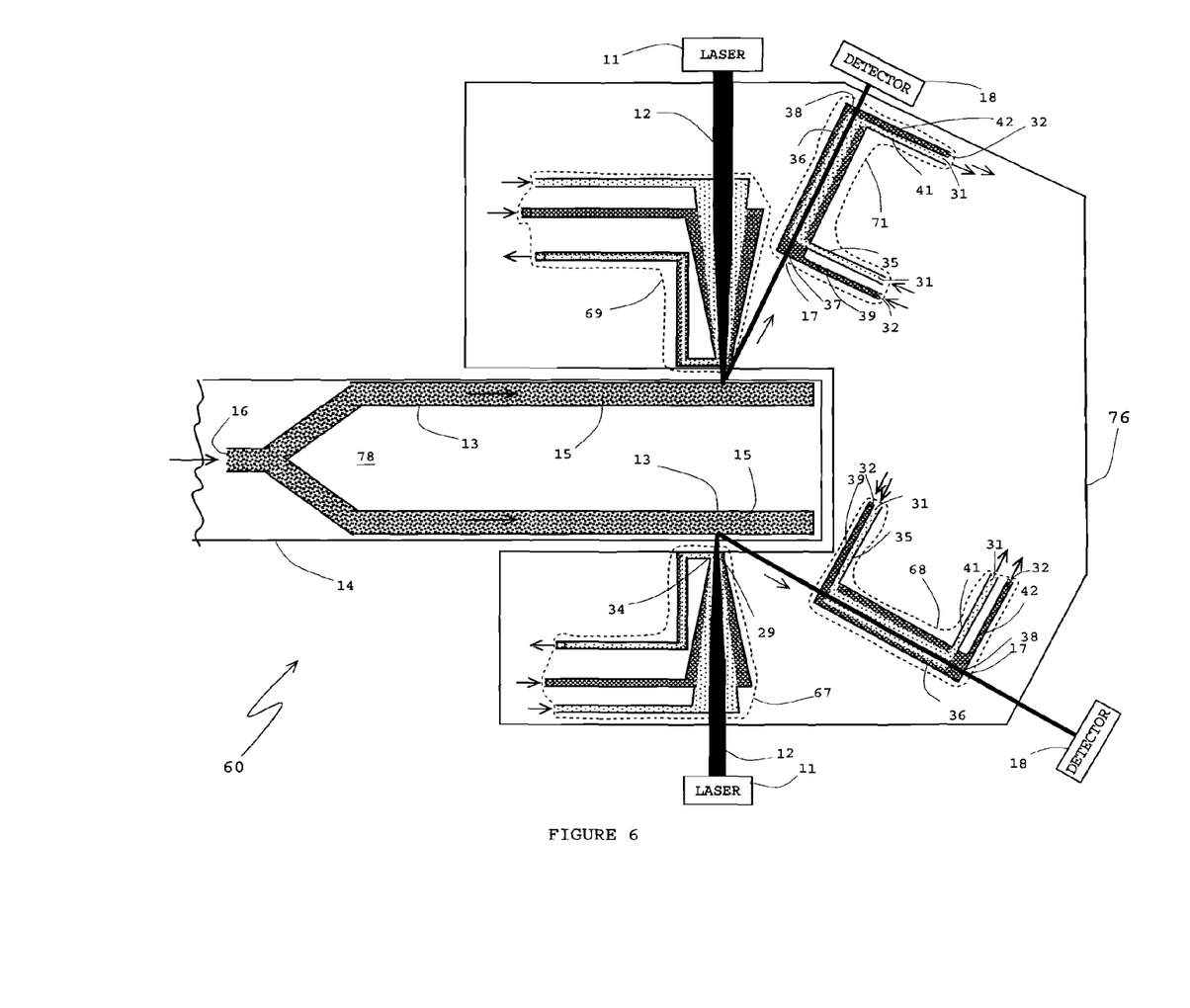
FIG. 6 shows an illustrative example of an on-card arrangement for fluid guiding of light to and from a dual flow channel with fluid guiding on another card.

FIG. 6 shows a system 60 that has sub-systems 67 and 68 like those of system 50 of FIG. 5 on a card 76 external to card 14. System 60 may have a dual channel 13 for a flow stream 16 of particles 15 for analysis with impinging beams 12 from lasers 11 projected on both channels and resultant light 17 scattered by the particles 15. The light 17 may be fluid-controlled by the sub-systems 68 and 71 and detected by the respective detectors 18. Light beams 12 may be fluid-controlled by sub-systems 67 and 69. Pumps and reservoirs for sub-systems 67, 68, 69 and 71 may be located on the card 76 or off the card.

Figure 7:
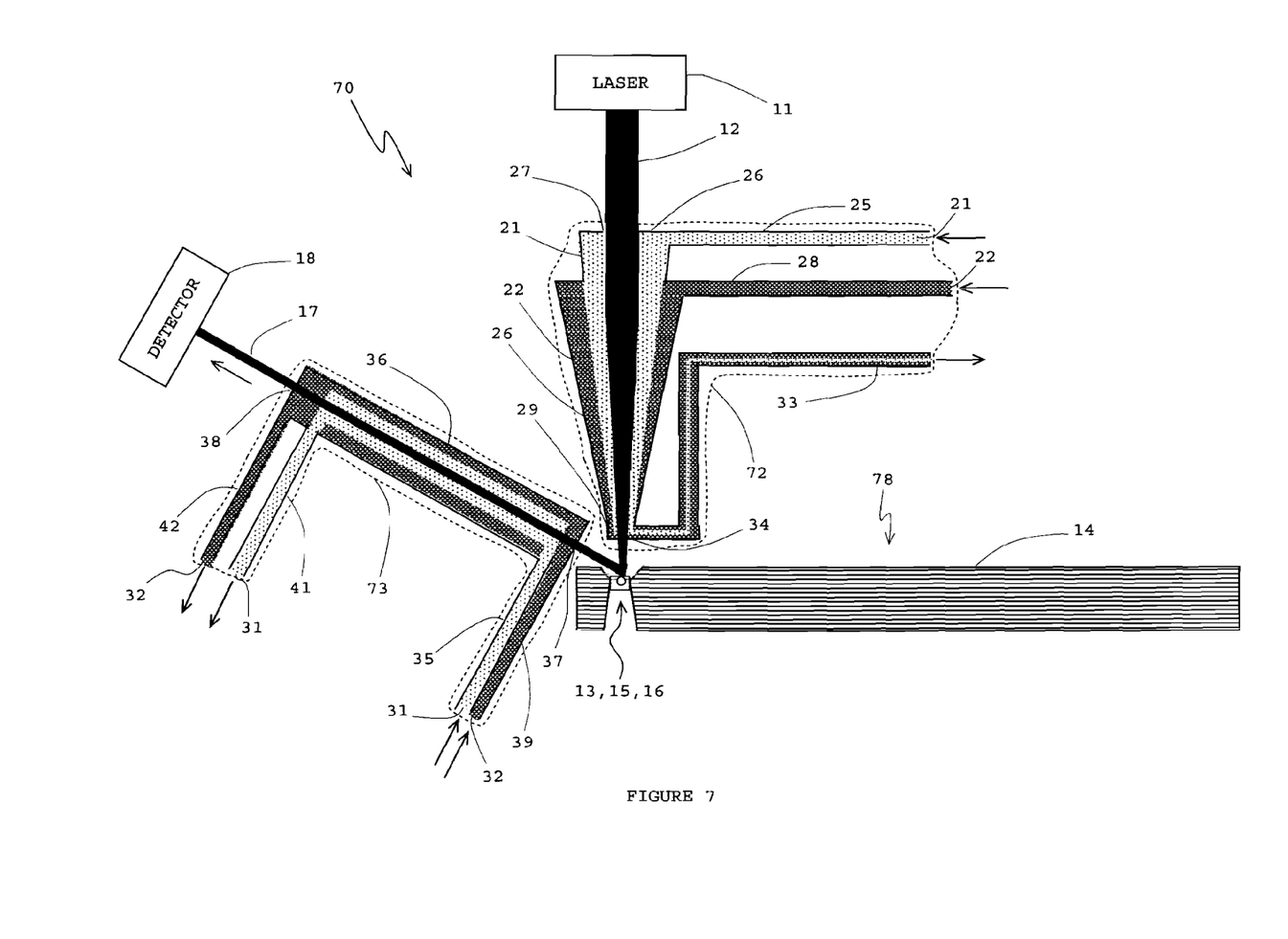
FIG. 7 shows an illustrative arrangement for fluid guiding of light to and from a flow channel approximately perpendicular to a larger surface side of a card.

FIG. 7 shows a system 70 that may have fluid-controlling sub-systems 72 and 73 for impinging light 12 to and scattered light from particles 15 in a flow stream 16 in an optical channel 13. A difference between the sub-systems 72 and 73 relative to the like sub-systems of systems 10, 20, 30, 40, 50 and 60 of FIGS. 1-6, respectively, is that they are not necessarily situated in a plane parallel to a plane of the card 14. The sub-systems 72 and 73 may be situated such that the impinging light 12 be directed to and the detected light 17 scattered by particles 15 in channel 13, are in a plane about perpendicular to the planar surface of card 14. Pumps and reservoirs for the sub-systems 72 and 73 may be situated proximate to these sub-systems.

Figure 8:
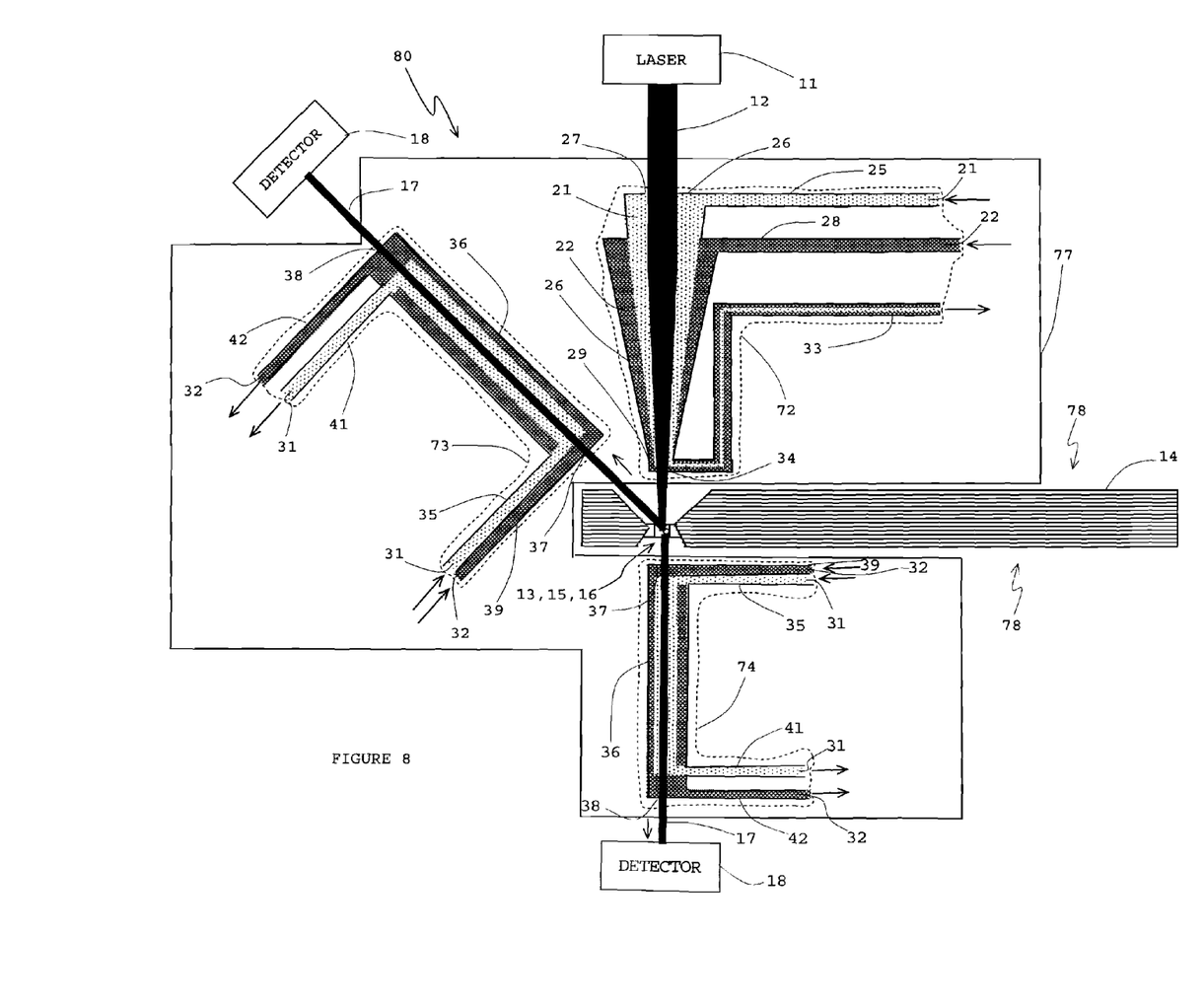
FIG. 8 shows an illustrative arrangement for fluid guiding of light to and from a flow channel to the larger surface side of a card with the fluid guiding on another but approximately perpendicular card.

FIG. 8 shows a system 80 having sub-systems 72 and 73 similar to those of system 70 of FIG. 7 for fluid control of the projected beam 12 and detected beam 17, to and from channel 13 of card 14, respectfully. The sub-systems 72 and 73 of system 80 may be different from those of system 70 in that they may be situated in or on a card 77 that is not in the same plane as the planar surface of card 14 or is approximately perpendicular to the planar surface of card 14. Another aspect of system 80 is that an additional detector 18 sub-system 74 may be situated to sense light 17 on the opposite side of the channel 13 which may be scattered or deflected by particles 15 in flow stream 16 or be straight through the channel 13. The angles for detection of the light 17 may various ones. Such angles may be non-perpendicular or perpendicular to the planar surface 78 of card 14. Pumps and reservoirs for the sub-systems 72, 73 and 74 may be on the card 77 or off-card.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. An analysis system comprising:
a cytometer flow channel having a target area;
a first fluid light guide having an output port aligned with the target area and an input port for being coupled to a light source; and
a second fluid light guide having an input port aligned with the target area and an output port for being coupled to a detector; and wherein:
each fluid light guide comprises fluids for guiding light;
the fluids comprise a first fluid and a second fluid;
the first fluid conveying light;
the second fluid containing the light; and
the first fluid being within the second fluid.

* * * * *